(12) United States Patent
Holmes et al.

(10) Patent No.: US 6,187,542 B1
(45) Date of Patent: Feb. 13, 2001

(54) METHODS FOR THE IDENTIFICATION OF PATIENTS AT RISK FOR HEART FAILURE

(75) Inventors: Edward Holmes, Durham, NC (US); Evan Loh, Merion Station, PA (US); Judith Swain, Stanford, CA (US)

(73) Assignee: The Trustees of the University of Pennsylvania, Philadelphia, PA (US)

( * ) Notice: Under 35 U.S.C. 154(b), the term of this patent shall be extended for 0 days.

(21) Appl. No.: 09/269,807

(22) PCT Filed: Oct. 3, 1997

(86) PCT No.: PCT/US97/17986

§ 371 Date: Nov. 24, 1999

§ 102(e) Date: Nov. 24, 1999

(87) PCT Pub. No.: WO98/14618

PCT Pub. Date: Apr. 9, 1998

Related U.S. Application Data

(60) Provisional application No. 60/027,582, filed on Oct. 3, 1996.

(51) Int. Cl.$^7$ .............................. C12Q 1/68; C12P 19/34; C07H 21/04
(52) U.S. Cl. .............................. 435/6; 435/91.2; 536/23.1
(58) Field of Search ...................... 435/6, 91.2; 536/23.1

(56) References Cited

U.S. PATENT DOCUMENTS 4,912,092 * 3/1990 Gruber ................................. 514/45

OTHER PUBLICATIONS

Morisaki et al. "Molecular basis of AMP deaminase defiency in skeletal muscle" Proc. Natl.Acad. Sci. USA 89:6457–6461.*
Loh et al., "Cardiac Transplantation in the 1990s", *Card. Rev.* 1, 218–227 1993.
Morisaki et al., "Molecular basis of AMP deaminase deficiency in skeletal muscle", *Proc. Natl Acad. Sci. USA* 1992 89, 6457–6461.

* cited by examiner

*Primary Examiner*—Stephanie Zitomer
*Assistant Examiner*—BJ Forman
(74) *Attorney, Agent, or Firm*—Law Offices of Jane Massey Licata

(57) ABSTRACT

A method of predicting the clinical outcome of patients suffering from congestive heart failure by identifying patients with a mutant allele of the AMPD1 gene is provided. Methods for increasing survival time in patients suffering from congestive heart failure by administering compositions which inhibit AMPD1 activity are also provided.

1 Claim, No Drawings

METHODS FOR THE IDENTIFICATION OF PATIENTS AT RISK FOR HEART FAILURE

This application claims the benefit of U.S. Provisional Application Ser. No. 60/027,582 filed Oct. 3, 1996 and PCT/US97/17986 filed Oct. 3, 1997.

INTRODUCTION

This invention was made in the course of research sponsored by the National Institutes of Health. The U.S. Government may have certain rights in this invention.

BACKGROUND OF THE INVENTION

Congestive heart failure is a complex clinical syndrome characterized by diminished cardiac contractile function and decreased exercise tolerance. Despite advances in medical therapy, 40% of patients die within one year of diagnosis and 70% are dead at five years.

A number of clinical predictors of survival in heart failure have been identified including age, decreased cardiac output and high blood pressure. However, clinical parameters alone have been of limited value in predicting survival in patients with congestive heart failure. It also appears that the genetic background of the individual plays a role. Accordingly, there is a need to identify genetic markers which are associated with improved or decreased survival in patients with heart failure.

The adenosine monophosphate deaminase 1 (AMPD1) gene is the predominant member of the AMPD multi-gene family expressed in adult cardiac myocytes and adult skeletal muscle. Approximately 20% of Caucasians and African Americans are heterozygous for a single mutant allele, AMPD1(+/−), which specifies a nonsense mutation in the second coding exon of this gene. This mutation leads to premature peptide chain termination and production of truncated peptide which is catalytically inactive. Deficiency in this enzymatic activity in myocytes resulting from the AMPD1 (+/−) genotype may have one of several metabolic consequences. A marked decrease in AMPD1 activity in myocytes may lower the adenylate energy charge in the myocyte by limiting deamination of AMP. A partial reduction in the activity of this enzyme may cause the myocyte to produce more adenosine following ATP catabolism. Increased adenosine production may be beneficial as adenosine is known to have potent cardioprotective effects. In patients with congestive heart failure, the residual cardiac myocytes experience greater metabolic demands; therefore, a reduction in AMPD activity may lead to increased adenosine production which could improve cardiac function.

Accordingly, compositions and methods which inhibit AMPD activity are desired. Further, methods of identifying patients who are likely to develop congestive heart failure and identifying those who may benefit from a cardiac transplant are also desired.

SUMMARY OF THE INVENTION

AMP deaminase activity has now been found to influence the clinical outcome in patients with heart failure. Patients with a mutant allele of the AMP deaminase 1 gene (AMPD1) have been found to have a significant prolongation of life if they develop congestive heart failure compared to patients without the mutant allele. Further, it has been found that patients who inherit at least one copy of this mutant allele, compared to patients who are homozygous for the wild-type allele, exhibit a longer duration of heart failure symptoms before requiring referral for cardiac transplant. Accordingly, it appears that one or more of the metabolic consequences of reduced AMPD activity provides for improved prognostic and survival advantages for individuals who inherit this AMPD1 mutant allele and subsequently develop heart failure. It is thus believed that reduction of AMPD activity in individuals suffering from congestive heart failure who are homozygous for the wild-type allele will improve the prognostic and survival advantages in these individuals.

Accordingly, an object of the present invention is to provide compositions and methods for inhibiting the AMPD1 enzyme and related enzymes from the AMPD1 gene family for the treatment of patients with congestive heart failure.

Another object of the present invention is to provide methods of predicting clinical outcome of patients suffering from congestive heart failure and identifying those patient most likely to benefit from a cardiac transplant which comprises identifying patients with a mutant allele of the AMPD1 gene.

DETAILED DESCRIPTION OF THE INVENTION

Congestive heart failure (CHF) is a common disorder which is often lethal in a very short period of time. Effective therapeutic options for treatment of this disease have been limited. However, it has now been found that in patients with CHF, the AMPD1 mutant allele is associated with prolonged survival after the onset of CHF symptoms.

Clinical data were collected on 132 consecutive patients (mean age 52.8±11.2 years) with advanced congestive heart failure. The patients were evaluated and a clinical database constructed which included medical history, physical examinations assessment of ventricular function and hemodynamics, and measurement of exercise capacity. Left ventricular fraction (LVEF) was determined by standard echocardiography or gated-blood pool analysis (MUGA). Cardiac output and hemodynamics were determined by the thermodilution technique in the cardiac catheterization laboratory. Exercise capacity was determined by a standard maximal exercise testing protocol with breath-by-breath, on-line expiratory gas analysis. These data were obtained at the time of initial evaluation and all patients were judged to be on optimal medical therapy for heart failure, including angiotensin-converting enzyme inhibitors, diuretics and digoxin at the time of this study. These patients were compared with two different control groups which included 91 and 416 normal volunteers without cardiovascular disease, respectively.

Genomic DNA was prepared from peripheral white blood cells from each subject. AMPD1 genotype was determined using a PCR based assay allele-specific oligonucleotide detection assay. In brief, genomic DNA was extracted from whole blood by rapid lysis technique and PCR-amplified in 1× PCR buffer and 1.25 U Taq polymerase. PCR primers were as follows: AMP 5'GCAATCTACATGTGTCTACC (SEQ ID NO: 1) and AMP 3'ATAGCCATGTTTCT-GAATTA (SEQ ID NO: 2). Thirty cycles consisting of 94° C. for 30 seconds (denaturation), 55° C. for 30 seconds (anneal) and 72° C. for 30 seconds (extension) were performed. PCR products were denatured and slot blotted in duplicate onto a nylon membrane along with positive and negative controls. The filter was hybridized with kinase labeled oligonucleotides representing the normal or the mutant sequence at nucleotide 34 of the cDNA. DNA from individuals heterozygous for the mutation at nucleotide 34 hybridized with both normal and mutant oligonucleotides.

The frequencies of the AMPD1 (+/+), AMPD1 (+/−) and AMPD1 (−/−) genotypes in patients with CHF and control groups were compared. Genotype frequencies were compared using Fischer's exact test between cases and controls. The mean and median duration of heart failure symptoms between the AMPD1 (+/+) and AMPD1 (+/−) (−/−) genotypes were determined. Analyses were performed to evaluate whether the duration of disease differed between the AMPD1 (+/+) and the AMPD1 (+/−) (−/−) genotypes using survival analysis techniques. Both Kaplan-Meier and Proportional Hazards models were fitted (Daniel, W. W. Applied Non-parametric Statistic, Second Edition. Boston: PWS-Kent Publishing Company (1990); and Shapiro, S. S. and Wilk, M. B. "An Analysis of Variance Test for Normality (Complete Subjects)". Biometrika 1965; 52:591–611). Only one CHF subject was homozygous for the mutant AMPD1 allele. For purposes of this study, the single AMPD1 (−/−) individual was included in the groups of heterozygous for the mutant allele; exclusion of this individual from the analysis did not alter the results of any statistical analyses. All continuous variable were calculated as mean±one standard deviation (S.D.)

The onset of heart failure symptoms was defined by the first hospital admission for the diagnosis of CHF. This date was established and verified by either retrospective chart review, direct patient interviews, and/or discussion with the referring physician by a single investigator blinded to the genotype of the patient. For the survival analyses, heart failure duration was defined as the duration of disease symptoms from first hospital admission for CHF to time of either cardiac transplantation, death, or the end of the study observation period. In addition, total disease duration was adjusted for age and sex prior to proportional hazards of Kaplan-Meier analysis by linear regression. Significance was established if the null hypothesis could be rejected at p value $\leq 0.05$.

At the time of referral for cardiac transplantation evaluation, the mean age of the 132 CHF patients was 52.8±11.2 years. The mean LVEF was 19.7%±6.7% and the mean peak $VO_2$ max was 13.9±4.9 ml/kg/minute. These values are consistent with New York Heart Association functional class II-IV heart failure symptomatology. Etiologies of CHF included: 1) coronary artery disease (n=69); 2) idiopathic cardiomyopathy (n=48); and 3) "other" (N=15, 4 valvular; 2 infiltrative; 3 congenital; 2 myocarditis; 4 alcohol). This distribution of clinical characteristics is very similar to most referral populations evaluated for cardiac transplantation (Loh et al. Card. Rev. 1, 218–227 (1993). No Asians were among these patients, an important exclusion since the AMPD1 mutant allele does, not appear to be present in this population (Morisaki et al. Proc. Natl Acad. Sci. USA 1992 89, 6457–6461). Of the 132 patients enrolled in the study, ill were homozygous for the wild-type allele (+/+), 20 were heterozygous (+/−), and one individual was homozygous for the mutant allele (−/−).

At the time of the initial evaluation, all patients exhibited severe, end-stage heart failure physiology (see Table 1). LVEF, cardiac index, pulmonary capillary wedge pressure, $VO_2$ max and pulmonary vascular resistance were not significantly different between CHF patients with the (+/+) versus (+/−)(−/−) genotypes.

TABLE 1

Clinical Characteristics of AMPD1 (+/+) vs AMPD1 (+/−) (−/−) Patients with Heart Failure

|  | AMPD1 (+/−) (−/−) (n = 21) | AMPD1 (+/+) (n = 111) |
|---|---|---|
| Age (yrs) | 56.8 ± 7.1 | 52.1 ± 11.6 |
| Gender |  |  |
| Male | 16 (79%) | 97 (89%) |
| Female | 5 (21%) | 14 (11%) |
| Etiology |  |  |
| CAD | 8 (38%) | 55 (50%) |
| IDCMP | 11 (52%) | 38 (34%) |
| Other | 2 (10%) | 18 (16%) |
| LVEF (%) | 18.9 ± 7.4 | 19.9 ± 6.9 |
| Cardiac index (1/min/m$^2$) | 1.8 ± 0.6 | 1.8 ± 0.8 |
| PCWP (mmHg) | 21.6 ± 10.9 | 22.0 ± 9.0 |
| PVR (Wood units) | 2.9 ± 2.1 | 2.9 ± 2.4 |
| VO$_2$ max (ml/kg/min) | 15.1 ± 6.7 | 13.7 ± 4.6 |
| Symptom duration (yrs) | 7.6 ± 6.5 | 3.2 ± 3.6* |

*p < 0.001 = AMPD1 (+/−) (−/−) vs AMPD1 (+/+)
all other comparison p > 0.05
all values = mean ± S.D.
AMPD1 (+/+): homozygous for wild-type allele
AMPD1 (+/−): heterozygous for mutant allele
AMPD1 (−/−): homozygous for mutant allele
CAD: coronary artery disease
IDCMP: idiopathic dilated cardiomyopathy
PCWP: pulmonary capillary wedge pressure
PVR: pulmonary vascular resistance
VO$_2$: maximal oxygen consumption The time from the first hospital admission for CHF symptoms to the clinical endpoint of death or cardiac transplantation was markedly different between AMPD1 (+/−)(−/−) and AMPD1 (+/+) patients, i.e. 7.6±6.5 years in AMPD1 (+/−) or (−/−) versus 3.2±3.6 years in AMPD1 (+/+) (p<0.0001) There was a trend for patients with a mutant AMPD1 allele to be older than the AMPD1 (+/+) homozygotes at the time of initial referral for cardiac transplantation evaluation. The mean age of AMPD1 (+/−) (−/−) patients was 56.8±7.1 years while the mean age of AMPD1 (+/+) patients was 52.1±11.6 years (p=0.07; t-test assuming unequal variances).

The difference in time or progression to end-stage CHF symptomatology and referral for transplantation evaluation is not explained by differences in etiology of heart failure or in gender between the genotypes (see Table 1). Further blinded chart reviews detected no differences in access to medical care, prescribed medical regimens or patient compliance.

However, Kaplan Meier analysis demonstrated that individuals with one or two mutant AMPD1 alleles live without transplantation for a significantly longer time after the first hospitalization for CHF symptoms than do patients homozygous for the wild-type allele. The proportional hazards model indicates a risk ratio of 4.65 (95% confidence interval: 1.67, 12.99) for age and sex-adjusted disease durations.

The frequency of AMPD1 genotype in heart failure patients was also determined. CHF patients were divided into two groups, those presenting within 5 years of the first hospitalization for CHF symptoms, and those presenting greater than 5 years after the first hospitalization for CHF symptoms. For the group that presented within 5 years from the first hospitalization for CHF, 7 of the 97 (16.7%) inherited the mutant AMPD1 allele. In the group that presented 5 years or later after the first hospitalization for CHF, 14 of the 35 inherited the mutant AMPD1 allele (43%).

Using the Mantel-Haenstel method of analysis, a patient carrying the AMPD1 mutant allele has an 8.6 odds ratio, relative to an individual homozygous for the wild-type allele, of living 5 or more years with CHF before requiring cardiac transplantation or dying.

When the AMPD1 genotype frequency of these two subgroups of CHF patients was compared to the group of normal volunteers, the CHF patients who presented less than 5 years after hospitalization for CHP were found to have a lower frequency of the mutant allele (16.7%) compared to the control population (25.3%). In contrast, CHF patients who presented 5 years or longer after the initial hospitalization for CHF demonstrated a trend towards a higher frequency of the mutant allele (43%) compared to the control population (25.3%). This finding is consistent with the AMPD1 mutant allele being a marker which identifies patients have a milder or more prolonged course of heart failure before requiring referral for consideration of cardiac transplantation.

Accordingly, in an embodiment of the present invention, a method for the identification of patients at risk for heart failure is provided. In this method, patients are tested to determine whether they carry the mutant AMPD1 allele. Those having a mutant allele of the AMPD1 gene have a significant prolongation of life if they develop congestive heart failure. Thus, those patients not carrying this marker are at a higher risk for heart failure and may require closer monitoring and more aggressive clinical interventions that those carrying the mutant allele. By identifying a patient's AMPD1 genotype, it is possible to select the most appropriate clinical treatment plan. Patients at the highest risk for heart failure can be identified and treated accordingly. The present invention thus provides a means for predicting and managing clinical outcome for patients with heart failure.

The present invention also provides a method and compositions for the treatment and, more specifically, the prolongation of survival in patients suffering from congestive heart failure who are homozygous for wild-type AMPD1. In humans, AMPD1 is the dominant member of a multigene family expressed in cardiac myocytes. Cardiac muscle has a very low level of AMPD enzyme activity; normal cardiac muscle has only 2% of the activity found in skeletal muscle. Prior studies have demonstrated that skeletal muscle from patients homozygous for the AMPD1 (−/−) allele have residual AMPD activity comparable to that found in normal heart. This low level of residual AMPD activity is associated with increased adenosine production following ATP catabolism in skeletal muscle.

Adenosine is a potent cardioprotective agent that enhances coronary flow, suppresses arrhythmias, induces the ischemic preconditioning response and suppresses cytokine production. These cardioprotective effects of enhanced adenosine production are believed to lead to increased survival in heart failure patients who carry at least a single copy of the mutant AMPD1 allele. Compositions and methods which enhance local adenosine production as a result of reduced AMPD1 activity would therefore be useful to patients with heart failure. Accordingly, it is believed that inhibitors of the AMPD enzyme will be useful for the treatment. and more specifically in the prolongation of survival in patients suffering from CHF. Further, even as little as a 50% reduction in the activity of the enzyme is expected to be beneficial.

Adenosine itself has not proven desirable for treatment of heart failure due to its very short in vivo half life (seconds). Further, adenosine must be administered by selective infusion into the coronary artery and often results in angina. Accordingly, inhibitors of the AMPD enzyme are preferred for the treatment of heart failure. The present invention provides compositions and methods for inhibiting the AMPD enzyme for the treatment of heart failure.

In accordance with the present invention, an effective amount of an AMPD inhibitor is administered to a patient with heart failure. By "effective amount" it is meant a concentration of a composition of the present invention which reducer the activity of the AMPD enzyme by at least 50%. Reduction of enzyme levels to 50% appears to be non-toxic based upon the general good health enjoyed by individuals heterozygous for the mutant AMPD1 allele. Concentrations of inhibitors to be administered can be routinely determined by those of skill in the art based upon the present disclosure and what is well known in the art. The inhibitors of the present invention may be administered in a pharmaceutically acceptable carrier. Suitable carriers are well known in the art and are selected in accordance with the intended route of administration and the standard pharmaceutical practice. For example, formulations for intravenous administration may include sterile aqueous solutions.

What is claimed is:

1. A method of predicting clinical outcome of patients suffering from congestive heart failure comprising:

a) obtaining a sample of peripheral white blood cells from a patient; and b) determining whether peripheral white blood cells from said patient have a nonsense mutation in the second coding exon of an adenosine monophosphate deaminase 1 gene wherein the presence of the mutant allele is predictive of clinical outcome in said patient.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 1
gcaatctaca tgtgtctacc                                                                    20

<210> SEQ ID NO 2
<211> LENGTH: 20
<212> TYPE: DNA
<213> ORGANISM: Artificial Sequence
<220> FEATURE:

-continued

<223> OTHER INFORMATION: Description of Artificial Sequence: Synthetic

<400> SEQUENCE: 2
atagccatgt ttctgaatta                    20